United States Patent [19]
Regnier

[11] 3,983,299
[45] Sept. 28, 1976

[54] BONDED CARBOHYDRATE STATIONARY PHASES FOR CHROMATOGRAPHY

[75] Inventor: Frederick E. Regnier, West Lafayette, Ind.

[73] Assignee: Purdue Research Foundation, W. Lafayette, Ind.

[22] Filed: Dec. 30, 1974

[21] Appl. No.: 537,197

Related U.S. Application Data

[63] Continuation-in-part of Ser. No. 447,640, March 4, 1974, abandoned.

[52] U.S. Cl. .................................. 428/405; 55/67; 55/386; 210/31 C; 210/198 C; 427/220; 427/301; 427/339; 427/399; 427/415; 428/406; 428/429
[51] Int. Cl.$^2$ ............................. B32B 17/02
[58] Field of Search ............... 55/67, 386; 210/31 C, 210/198 C; 427/220, 301, 339, 399, 415; 428/405, 429, 406

[56] References Cited
UNITED STATES PATENTS

| | | | |
|---|---|---|---|
| 2,446,119 | 7/1948 | White et al. | 427/385 |
| 2,787,518 | 4/1957 | Hiler | 427/171 |
| 2,950,985 | 8/1960 | D'Adrian | 427/180 |
| 2,953,478 | 9/1960 | Harvey et al. | 428/273 |
| 3,481,771 | 12/1969 | Doering | 428/392 |
| 3,673,150 | 6/1972 | Marzocchi | 428/392 |
| 3,677,938 | 7/1972 | Le Page et al. | 210/31 C |
| 3,722,181 | 3/1973 | Kirkland et al. | 210/31 C |
| 3,808,125 | 4/1974 | Good | 210/31 C |
| 3,840,464 | 10/1974 | Van Engeland | 252/62.1 |

FOREIGN PATENTS OR APPLICATIONS

| | | | |
|---|---|---|---|
| 25,610 | 1971 | Japan | 428/405 |

Primary Examiner—Ronald H. Smith
Assistant Examiner—Dennis C. Konopacki
Attorney, Agent, or Firm—John R. Nesbitt

[57] ABSTRACT

A carbohydrate bonded support for use in a chromatographic system, and a method for preparation of such a support is disclosed herein. An inorganic support has a thin layer of carbohydrate or carbohydrate derivative covalently linked to the surface so that the thus formed support has excellent mechanical stability as well as the ability to avoid adsorbing or denaturing sensitive biological compounds, the carbohydrate bonded support thus combining the advantages of known supports without also incorporating the disadvantages thereof.

21 Claims, 4 Drawing Figures

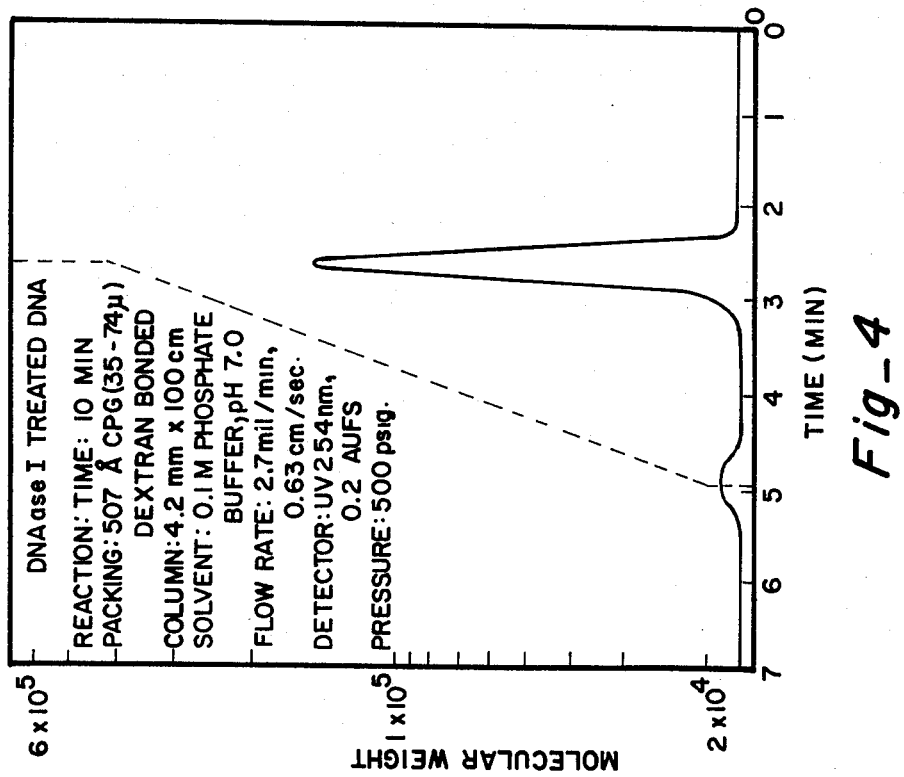
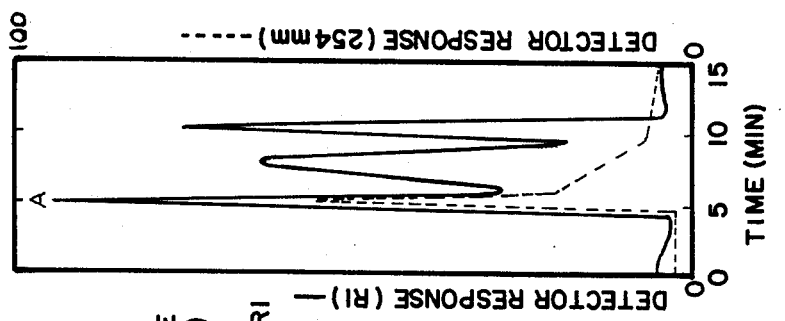

BONDED CARBOHYDRATE STATIONARY PHASES FOR CHROMATOGRAPHY

RELATED APPLICATION

This application is a continuation-in-part of copending U.S. application Ser. No. 447,640, filed Mar. 4, 1974 and entitled "Bonded Carbohydrate Stationary Phases For Chromatography" and now abandoned.

FIELD OF THE INVENTION

This invention relates to a carbohydrate bonded support, and more particularly relates to a carbohydrate bonded support for a chromatographic system.

BACKGROUND OF THE INVENTION

The use of supports in chromatographic systems is well known, as is the use of such systems for the chromatography of biological compounds, such as proteins, nucleic acids, viruses, and dextrans.

Heretofore, it has become common to use an inorganic support in chromatographic systems since such supports commonly provide good mechanical stability. Inorganic supports commonly utilized are, for example, glass, silica or alumina. With the advent of high speed chromatography, supports providing good mechanical stability have become increasingly important since such supports must withstand the relatively high pressures encountered in this type of chromatography. Inorganic supports, however, while providing good mechanical stability, often adversely affect at least some biological compounds and hence are not suitable for use with such compounds. By way of example, inorganic supports such as silica or glass beads denature or adsorb many enzymes. Obviously, while inorganic supports have proved useful due to the mechanical stability provided, the use of chromatographic systems including such supports has been seriously limited due to the adverse effect of such supports upon many biological compounds.

Carbohydrates have also been used extensively as supports and stationary phases in chromatographic systems. An early use was in the paper chromatographic separation of amino acids. In this type of separation, the cellulose of paper adsorbs the more polar components of the solvent system and acts as a stationary phase support for liquid-liquid partition separations.

Later it became known that carboxymethyl and diethylaminoethyl derivatives of cellulose could be used in the ion exchange purification of compounds. In this type of separation, water causes the cellulose to swell into a matrix into which protein may diffuse. Ion exchanging groups covalently linked in this matrix then partition molecules on the basis of their charge.

Still later, it became known that polysaccharides could be used in the preparation of steric exclusion and affinity chromatography columns. The ability of carbohydrate to imbibe water and the ease with which derivatization reactions could be carried out in polysaccharide matrices were again important factors in their selection.

Finally, gas chromatography columns have been prepared by coating solid supports with monosaccharides such as mannitol and sorbitol. At the present time, carbohydrates or carbohydrate derivatives have been used successfully in the preparation of gas, liquid-liquid partition, ion exchange, steric exclusion, and affinity chromatography columns.

The success of carbohydrates as chromatographic supports is based primarily upon: the ability of carbohydrates to imbibe large quantities of polar solvents which act as a stationary phase and cause the carbohydrate to swell into a hydrophilic matrix; the chemical stability of the formed hydrophilic matrix and the ease with which it is derivatized with ion exchange groups, ligands, and specific functional groups; and the ability of carbohydrates to stabilize sensitive biological compounds such as proteins.

The use of carbohydrates as a support, however, did not prove to be satisfactory for all uses since the carbohydrate support was found to have low mechanical stability. Where attempts were made to achieve more rapid analysis by increasing the flow rate of carbohydrate columns, the resulting higher pressures caused the bed to collapse. Thus, the primary objection to current carbohydrate supports is that analysis times are too long, and hence such supports are not suitable for high speed chromatographic systems.

For high speed chromatographic systems, the currently accepted technique for decreasing analysis time is to pump liquid through columns. Modern high speed liquid chromatography columns packed with silica or glass (inorganic) supports are capable of withstanding pressures of 300 to 400 atmospheres and flow rates 50 to 100 times greater than carbohydrate columns. But as brought out hereinabove, while silica and glass particles have good mechanical stability, they lack many of the desirable characteristics of carbohydrates such as, for example, the ability of carbohydrates to handle proteins without adsorbing or denaturing the same.

Heretofore, however, no support has been suggested or utilized that combines both good mechanical stability and superior separation characteristics in handling compounds such as biological compounds to provide a chromatographic system that offers quality of performance with minimum time requirements.

SUMMARY OF THE INVENTION

This invention provides an improved support for chromatographic systems that provide excellent dimensional stability with minimum adsorption and denaturation of biological compounds during separation. The support is formed by covalently linking a thin layer of carbohydrate or carbohydrate derivative to the surface of an inorganic support through an organosilane to thereby gain the advantage of both without incorporating the disadvantages of either. The inorganic supports are materials having available surface oxide or hydroxyl groups. They may be classified as silaceous materials or nonsilaceous metal oxides. The silaceous materials consisted of either controlled porosity glass (Corning Glass Works Code 7930) or controlled porosity silica (EM Laboratories Code SI 200 A). Porous Alumina (Corning Glass Works) was the only nonsilaceous material used.

The silane coupling agents contain an organic-functional moiety and a silicone-functional species. The silicone-functional species reacts rapidly with inorganic surfaces and grafts the organic moiety to the surface of inorganic supports. The organic portion of the silane coupling agent either contains a carbohydrate or will react readily with a carbohydrate derivative to bond it to the support. The primary function of the coupling agent is to provide a bond between the carbohydrate and the inorganic support. The main function of the carbohydrate is to function as a stationary phase in the chromatographic system. The chromatographic properties of the support will be determined by the nature of the carbohydrate bonded phase. Thus, the bonded phase support in this invention provides column packing materials for a chromatographic system that has the excellent dimensional stability under pressure of inorganic supports while at the same time having the superior separation properties of carbohydrates.

It is therefore an object of this invention to provide an improved support for chromatographic systems.

It is another object of this invention to provide an improved support having excellent dimensional stability and superior separation properties.

It is still another object of this invention to provide an improved support for high speed chromatographic systems that provides quality of performance.

It is yet another object of this invention to provide an improved support that does not adsorb or denature biological compounds and yet provides good mechanical stability. This is accomplished by deactivation of surface charges.

It is still another object of this invention to provide a carbohydrate bonded support.

It is another objective of this invention to provide a thin neutral organic layer that excludes sensitive compounds from contact with the surface of the support.

It is another object of this invention to form a support by bonding a thin layer of carbohydrate on an inorganic support.

It is yet another object of this invention to form a support by covalently linking a thin layer of carbohydrate to the surface of a substance having a surface rich in hydroxyl groups.

It is yet another objective of this invention to provide a bonded organic layer on the inorganic support that imbibes water and creates a hydrophilic surface layer in the pores of the support.

It is still another object of this invention to provide an improved method for forming a support for chromatographic systems.

With these and other objects in view which will become apparent to one skilled in the art as the description proceeds, this invention resides in the novel support and method for forming the same substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

FIGS. 2 and 3 illustrate the use of a glycerol bonded CPG support for separation of a mixture of nucleic acids and mixtures of dextrans and glucose, respectively; and FIG. 4 illustrates the use of a CPG dextran bonded support for resolution of nucleic acids.

DESCRIPTION OF THE INVENTION

Figure 2:
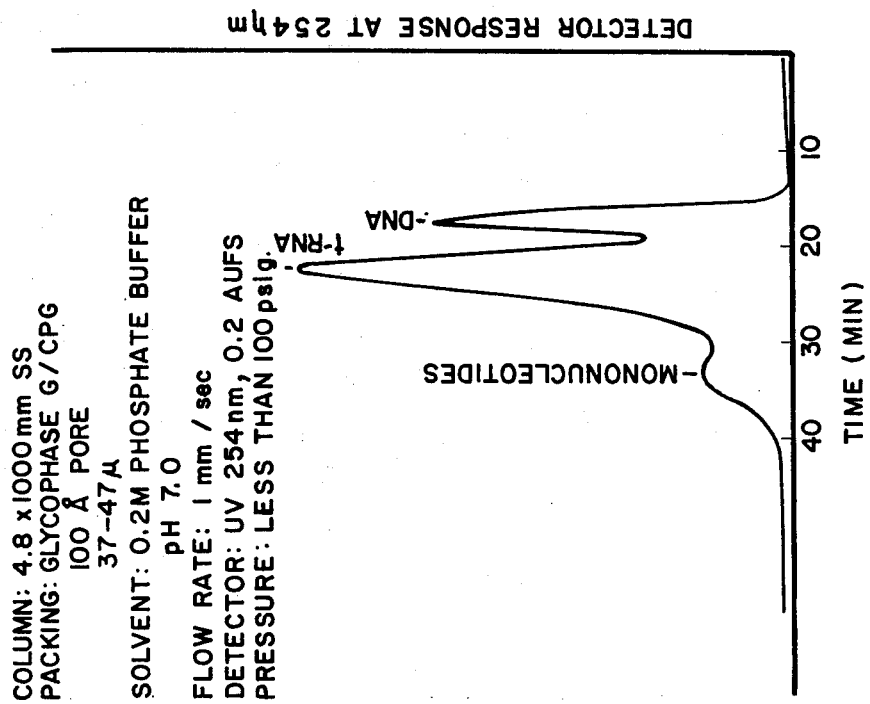

A thin layer of carbohydrate is bonded to the surface of a silaceous (silica or glass) or nonsilaceous (alumina) inorganic support to form chromatography stationary phases that show excellent dimensional stability under pressure and the separation characteristics of a carbohydrate support.

All covalent linkages of organic compounds to inorganic supports were made through hydroxyl groups on the supports by known coupling reactions. The reagents employed in coupling carbohydrates to the surface of inorganic materials are commercially available and have the general formula:

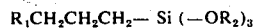

$$R_1CH_2CH_2CH_2—Si(—OR_2)_3$$

wherein $R_1$ is either a carbohydrate or an organic functional group that reacts readily with a carbohydrate or carbohydrate derivative and $—OR_2$ is an alkoxide.

The coupling agent is applied to the inorganic support from a toluene solution. Refluxing the solution from 4–12 hours provides adequate bonding of the coupling agent. The thin layer of carbohydrate bonded to the surface of the support structure is preferably less than about 30 Å.

The types of bonding between coupling agents and carbohydrates are described in the equation below ( ≡ as used hereinafter refers to the three silicon bonds to the surface. Such bonds are also shown, for example, in U.S. Pat. No. 3,722,181):

1. Ether bonding:

$$\equiv Si(CH_2)_3OCH_2CH\overset{O}{\overset{\diagup\diagdown}{\phantom{xx}}}CH_2 \xrightarrow[30\ min.]{H^+ \cdot H_2O} \equiv Si(CH_2)_3OCH_2\overset{OH}{\underset{|}{C}}H—\overset{OH}{\underset{|}{C}}H_2$$

Reaction Scheme 1

2. Amine bonding:
   a. Coupling through terminal aldehyde in dextran

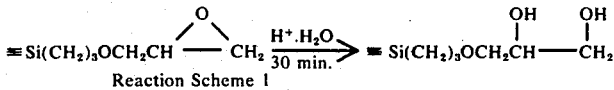

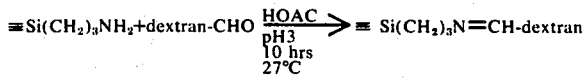

Reaction Scheme 2 b. Coupling of dialdehyde starch

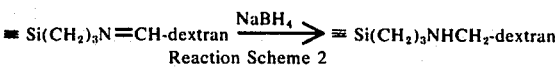

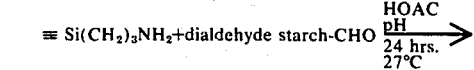

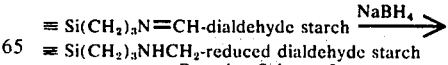

Reaction Scheme 3 c. Coupling through epoxides

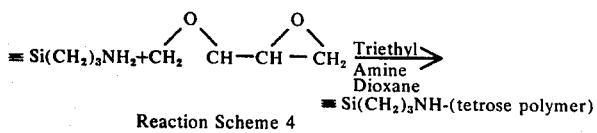

Reaction Scheme 4

3. Amide bonding:

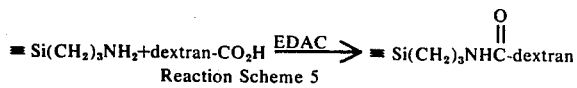

Reaction Scheme 5

4. Isourea bonding:

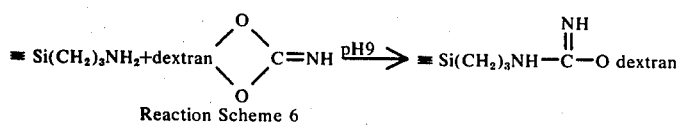

Reaction Scheme 6

Inorganic supports to which carbohydrates have been successfully bonded are porous silica, controlled porosity glass (CPG), controlled porosity ceramic, and alumina. It is probable, however, that carbohydrates may be bonded to any inorganic support containing a high surface density of hydroxyl groups. Carbohydrates bonded to at least one inorganic support have been glycerol ethers, tetrose ethers, sorbitol, starch, dextrans, carboxymethyl dextrans, and polygalactan.

Since the predominant problem in the chromatography of biological macromolecules on inorganic supports is solute adsorption of denaturation, testing of carbohydrate bonded supports centered around the prevention of these phenomena. It is common to chromatograph proteins with enzymatic activity on inorganic steric exclusion chromatography supports. The undesirable loss of biological activity encountered with these inorganic supports may be quantitated in a static assay using enzymes. The recovery of enzymatic activity after one hour incubation at 27°C of 1 ml of enzyme solution with 100 mg of inorganic support gives a direct measurement of what any given support will do to a biological molecule.

Alkylamine derivatives of controlled porosity glass beads may be commercially obtained, as for example, from Corning Glass Works, Medfield, Massachusetts. Alkylamine silica supports may be prepared by treating the beads with a 10% aqueous solution of γ-aminopropyl triethoxysilane at pH 4 for 2 hours at temperature of 90°C. After silylation, the particles may be washed with water, ethanol and diethyl ether and then placed in a vacuum (10 mm) for 18 hours.

The following examples set forth methods of covalently linking carbohydrates and carbohydrate derivatives to solid supports:

EXAMPLE I

Preparation of "Glycerol" bonded CPG Packing for Liquid Chromatography.

Twenty-five grams of 507 A pore diameter controlled porosity glass (CPG, 200/400 mesh) were treated at 100°C for 4 hours with a solution containing 90 ml of toluene and 10 ml of glycidoxypropyl trimethoxysilane. The suspension was then filtered and washed with 100 ml volumes of ethanol and water. The epoxide was converted to the diol by a 30 minute treatment at pH 2. After a final wash with water and ethanol the glycerol-bonded support was dried in vaccuo. The synthetic scheme and structure of this support are shown in Reaction Scheme 1 above.

Elemental analysis of the resulting "glycerol" bonded phase showed that 1.2% of the bonded CPG was organic. Periodate oxidation indicated the presence of 0.8 meq. of diol/gram of CPG.

Figure 1:
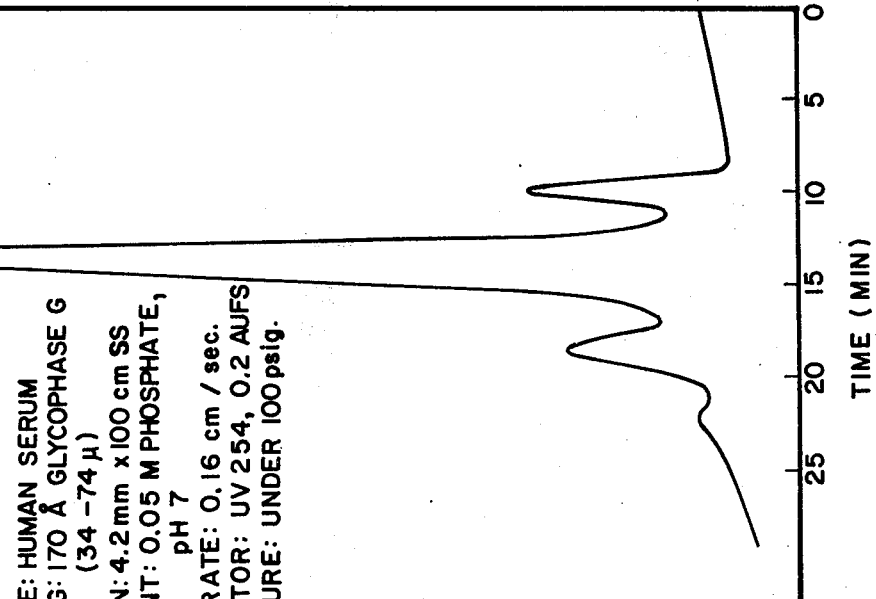
FIG. 1 illustrates a typical steric exclusion separation of proteins utilizing a glycerol bonded CPG support.

A typical steric exclusion separation of proteins on a 170 A pore diameter "glycerol" bonded CPG support is shown in FIG. 1. Support particles of 38-74μ were packed into a 4.2 mm × 100 cm column and used to separate a mixture of serum proteins in 25 minutes. The column was eluted with 0.05 M phosphate buffer (pH7) at a flow rate of 0.16 cm/sec and a column pressure of 100 psig. Compounds were detected with an ultraviolet detector.

Nucleic acids may similarly be separated on "glycerol" bond supports. A 4.8 mm × 100 cm column packed with 100 A "glycerol" bonded 38-74μ CPG was used to separate a mixture of nucleic acids in 35 minutes (see FIG. 2). The column was eluted with 0.2 M phosphate buffer (pH 7) at a flow rate of 0.1 cm/sec and a column pressure of 100 psi. Polysaccharides may also be separated on the "glycerol" bonded support. A 2.0 mm × 120 cm column packed with 100 A "glycerol" bonded 38-74μ was used to separate a mixture of dextrans and glucose as shown in FIG. 3. The column was eluted with 0.1 M phosphate buffer (pH 7) at a flow rate of 4 mm/sec. and a column pressure of 400 psig. Peak A in FIG. 3 is 2,000,000 M.W. dextrans and peak C is glucose.

The "glycerol" bonded CPG has been found to have good chemical and mechanical stability at both high mobile phase velocities (5 cm/sec) and pressure (3000 psi).

The separation characteristics of this "glycerol" bonded support were very similar to those of the initial controlled porosity glass when compared in the steric exclusion chromatography of chymotrysin. The distribution coefficient ($K_d$) on the "glycerol" bonded supports was 0.80 while the $K_d$ on CPG was 0.82. This represented a change of approximately 30 A (6%) in the pore diameter of the CPG. Since a monolayer of glycerolpropyl silane would theoretically decrease the pore diameter by 28 A, the experimental and theoretical calculations were deemed to be in agreement.

Static assays of the recovery of enzymatic activity with several different enzymes are shown in Table I for both "glycerol" bonded CPG and native CPG. It will be seen that in all cases, the "glycerol" bonded support yields a recovery of activity that is equal to or greater than CPG.

TABLE I

Relative Recovery of Enzymes from Various Materials (%)
Static (Incubation) Conditions

| Enzymes | "Glycerol" Bonded CPG | Uncoated CPG |
| --- | --- | --- |
| Chymotypsin | 96% | 16% |
| Lactic Acid Dehydrogenase | 100 | 23 |
| Lipoxygenase | 95 | 8 |
| Alpha Keto Arginine Decarboxylase | 100 | 100 |
| Anthranilate Synthetase | 91 | 49 |
| DAHP Synthetase | 96 | 2 |
| Pyrophosphatase (Corn Leaf) | 100 | 93 |
| Threonine Deaminase | 79 | 34 |
| Dihydroxy Acid Dehydratase | 90 | 51 |
| Acetohydroxy Acid Synthetase | 95 | 95 |
| Isomero Reductase | 100 | 62 |

Test Conditions
100 mgs CPG
Enzyme ($10^{-6}$ M or lower) in phosphate buffer (pH 7)
Incubated 1 hour at R.T.

It is clear that "glycerol" bonded CPG is superior to native CPG in preventing loss of enzyme activity during solution contact.

EXAMPLE II

Preparation of "Dialdehyde Starch"/CPG Bonded Phase.

Dialdehyde starch (M.W. 1500) and dialdehyde dextrans (M.W. 3500, 6000, and 10,000) were prepared as described in the literature. These dialdehyde carbohydrates will be referred to as DAS 1.5, DAD 3.5, DAD 6, DAD 10, and DAD 20 respectively. The dialdehyde carbohydrates were coupled to alkylamine supports through schiff base formation. Two grams of 550 A pore diameter alkylamine CPG (80/120 mesh) were treated with 2 grams of dialdehyde carbohydrate in 50 ml of 1 M acetate buffer (pH 3) for 4 hrs. at 27°C. Following filtration, the schiff base coupled carbohydrate was reduced with 0.5 g of $NaBH_4$ in 10 ml of water. After filtration, the secondary amine coupled support was finally washed with water and ethanol before drying. The synthesis and structure of this support is shown in Reaction Scheme 3 above.

Static assays of the recovery of enzyme activity from chymotrypsin are shown in Table II.

TABLE II

| Support | Chymotrypsin Recovery |
| --- | --- |
| Reduced DAS 1.5 on CPG | 79% |
| Reduced DAD 6 on CPG | 71% |
| Reduced DAD 10 on CPG | 53% |

Ninhydrin determinations on the reduced dialdehyde carbohydrate bonded supports indicated that at least 90% of the initial alkylamine on the surface of the alkylamine glass had not participated in the coupling reaction. No attempt was made to determine the amount of carbohydrate that was bound to the glass.

EXAMPLE III

Preparation of "Tetrose Amine"/CPG Bonded Phase.

Two grams of 550 A pore diameter alkylamine CPG (80/120 mesh) were treated at 100°C for 12 hrs with dioxane containing 2% butadiene diepoxide. Following filtration the glass was washed with ethanol and water and treated at pH 2 for 30 min. The final treatment with acid converts epoxides to diols. After a final water and ethanol wash, the support was dried. The synthesis of this material is outlined under Reaction Scheme 4.

The recovery of enzymatic activity from chymotrypsin in a 1 hr. static assay with this tetrose derivative was 96% as opposed to 16% for native CPG. Ninhydrin analysis on the derivatized support showed no free primary amine and indicated that the surface of the glass has been fully derivatized. From the standpoint of enzyme recovery, the tetrose-bonded support is superior to native CPG.

Two grams of 440 A pore diameter controlled porosity ceramic were also derivatized with butadiene diepoxide. The static recovery assay with chymotrypsin was the same as with tetrose derivatized CPG.

The same procedures used above for coupling butadine diepoxide were used to couple diglycidoxy ethylene glycol and diglycidoxy butanediol to inorganic supports in the synthesis of "glycerolamine" supports. The properties of these bonded supports appeared to be slightly inferior to the tetrose bonded support in static enzyme recovery assays.

These "tetrose amine" and "glycerol amine" bonded supports function as weak anion exchangers in chromatography columns. Human serum proteins may be resolved in a gradient elution with phosphate buffers ranging from 0.01M (pH 8) to 0.4M (pH4). A 550 A pore diameter "tetrose amine" support has a hemoglobin ion exchange capacity of approximately 20 mg/ml of support.

EXAMPLE IV

Preparation of "Dextran"/CPG Bonded Phase.

Both hexoses and polysaccharides were bound to alkylamine supports through the isourea linkage as outlined in Reaction Scheme 6. Carbohydrates were activated by treating them with CNBr at pH 10 for 2 hrs as described in the literature. Coupling of the CNBr activated carbohydrate was achieved at pH 10 in less than an hr by adding the carbohydrate solution to an alkylamine support. Two grams of alkylamine support (usually 550 A pore diameter CPG) were used in these experiments. The molar ratios of reactants for a series of carbohydrates are shown in Table III. After the coupling reaction was complete, the carbohydrate-bonded support was washed with water and ethanol before drying.

TABLE III

| Compound | Molar Ratio of Reactants CNBr/monosaccharide residue | Carbohydrate/alkylamine |
|---|---|---|
| Dextran (M.W.=40,000) | 0.1 | 1 |
| Dextran (M.W.=10,000) | 0.1 | 2 |
| Dextran (M.W.=6,000) | 0.1 | 3.3 |
| Dextran (M.W.=6,000) | 1.0 | 3.3 |
| Starch (M.W.=1,500) | 0.1 | 12 |
| Sorbitol | 1.0 | 120 |
| Polygalactan | 0.1 | 2 |

The adsorption of $5 \times 10^{-6}$ M chymotrypsin on these supports was determined in static assays by measuring the disappearance of protein from the incubation medium. The adsorption of chymotrypsin of carbohydrate bonded supports is seen in Table IV.

TABLE IV

| Preparation | % Adsorption |
|---|---|
| CPG (native) | 100 |
| CPG-alkylamine | 93 |
| CPG-sorbitol | 75 |
| CPG-starch (M.W.=1,500) | 0 |
| CPG-Dextran (M.W.=40,000) | 33 |
| CPG-Dextran (M.W.=10,000) | 25 |
| CPG-Dextran (M.W.=6,000) | 0 |

When the bonded CPG-starch (M.W.=1,500) was static assayed with a series of enzymes for recovery of activity, the results in Table V were obtained.

TABLE V.

| Enzyme | % Recovery CPG-Starch | CPG |
|---|---|---|
| Chymotrypsin | 89 | 16 |
| Lactic Dehydrogenase | 82 | 23 |
| Alcohol Dehydrogenase | 58 | 4 |
| Lipoxygenase | 44 | 8 |
| Pyrophosphatase | 100 | 93 |

Quantitative periodate oxidation of M.W. 1,500 starch bound to 550 A alkylamine CPG (80/100 mesh) indicated starch loading ranging from 11 to 16 mg/g CPG. This would be from 7.6 to 10.8 $\mu$ moles of starch/gram of CPG. The variation in carbohydrate loading is primarily dependent on the amount of amine on the surface of alkylamine support.

The use of the 3,500 molecular weight "Dextran"/CPG support in the steric exclusion resolution of nucleic acids is shown in FIG. 4. This sample was prepared by treating DNA with deoxyribonuclease I. The column was 4.2 mm × 100 cm packed with 507 A pore diameter support (35–74$\mu$) and eluted with 0.1 M phosphate buffer (pH 7) at 0.63 cm/sec.

EXAMPLE V

Preparation of "Sorbitol Acetate"/CPG Bonded Phase.

25g of CPG-sorbitol (400 A, 200/325 mesh) prepared according to Example IV were acetylated with 100 ml of a 1:1 acetic anhydride pyridine mixture. After filtration, the support was washed with ether and dried. A 4 mm × 1 m column packed with this sorbitol acetate bonded phase support was used to separate a mixture of benzene, acetophenone and phthalic anhydride. The column was developed with a hexane:chloroform (3:1) solvent mixture. The retention times of benzene, acetophenone, and phthalic anhydride were 1.5, 4, and 8.5 min. respectively. It may be concluded that this bonded phase support will function for liquid-liquid partition chromatography in non-aqueous systems.

A ⅛×18 inch gas chromatography column was packed with the sorbitol acetate packing described above. The column was temperature programmed from 180° to 250°C. The test mixture consisted of n-octane, n-nonane, n-decane, n-undecane, n-dodecane, n-tridecane, and 1-tridecene. Complete resolution of all saturated hydrocarbons was achieved in 20 min with partial resolution of n-tridecane and 1-tridecene.

EXAMPLE VI

Preparation of Terminal Aldehyde Coupled "Dextran"/CPG Bonded Phase.

Dextran with a terminal aldehyde functional group was coupled to 400 A pore size alkylamine CPG (120/200 mesh) by treating with 100 ml of a pH 3 10% aqueous solution of 10,000 M.W. dextran at 100°C. After filtration, the schiff base coupled carbohydrate was reduced with 0.5 g of NaBH$_4$ in 20 ml of water. After filtration and washing with ethanol, the support was dried. This support was prepared according to Reaction Scheme 2.

One hour static adsorption assays with $5 \times 10^{-6}$ chymotrypsin indicated that the above support adsorbed 41% of the enzyme while native CPG and alkylamine CPG adsorbed 100% and 93% of the enzyme respectively.

EXAMPLE VII

Preparation of Terminal Carboxyl Coupled "Dextran"/CPG Bonded Phase.

Amide coupling of carbohydrates to inorganic supports was achieved by binding a carboxyl containing carbohydrate to an alkylamine support. In these experiments, the terminal carbonyl group of M.W. 10,000 dextran was oxidized to the carboxylic acid as described in the literature. Amide bond formation with the alkylamine support was achieved with the water soluble carbodiimide EDAC. 1 gram of 400 A pore diameter CPG was treated with a 50 ml solution containing 1 gram of carbohydrate and 200 mg of EDAC at pH 4.7 and 27°C for 12 hrs. The synthesis of this phase is described in Reaction Scheme 5 above.

A static adsorption assay with $5 \times 10^{-6}$ M chymotrypsin showed that this material adsorbed 45% of the enzyme protein in one hr.

EXAMPLE VIII

Preparation of "Carboxymethyl Dextran"/CPG Bonded Phase.

In further experiments on amide coupled carbohydrate phases, carboxymethyl dextran (M.W.=10,000) was synthesized and coupled to alkylamine supports by the technique described in Example VII. Since there are a large number of carboxyl groups on carboxymethyl dextran, excess carboxyl groups remain after the coupling reaction.

A 4 mm × 1 m column was packed with this carboxymethyl dextran bonded support (368 A, 375/400 mesh) and used in the separation of the proteins contained in a crude soybean trypsin inhibitor preparation. The gradient elution development with $5 \times 10^{-3}$ M pH 4 acetate buffer solution ranging from 0.0 to 0.8 M NaCl resolved the components of the mixture in an elution profile similar to that described for carboxymethyl cellulose in the literature. The basic difference with the carboxymethyl dextran bonded support was that the total elution time for all proteins was 7 min. We have been able to operate this column at 2500 psig and up to 10 times higher flow rates than conventional carbohydrate columns.

A carboxymethyl ion exchange support was also prepared by a second synthetic route. Ten grams of "glycerol" bonded support (Example I) was treated with 10 μmoles of aqueous sodium periodate for 24 hrs. followed by filtration and treatment with 0.2 μmoles of potassium permanganate for 1 hr. Final filtration and washing with sodium bisulfite yielded the "carboxymethyl" ion exchanger. The 250 A "carboxymethyl" ion exchange support had a hemoglobin ion exchange capacity of 40 mg hemoglobin/cc of support. A 1.5 × 20 cm column packed with 250 A (74–128μ) ion exchange support purified the protein myoglobin when developed with 0.02 M phosphate buffer (pH 6.9).

EXAMPLE IX

Preparation of "Hydrophobic Dextran"/CPG Bonded Phase.

Dextran (T-10) bonded phase (Example IV) 37–74μ particle size (470 A) controlled porosity glass was cyanogen bromide activated at pH 10 and allowed to react with octylamine. The resulting octylamine dextran bonded phase was used in the hydrophobic chromatography of proteins. The test mixture utilized was a mixture of glycyltyrosine, chymotrypsin and the protein ovalbumin. When a one meter column was developed with 0.5 M phosphate buffer and 1 M NaCl at pH 7, glycyltyrosine, chymotrypsin and ovalbumin were all eluted in that order. For utilization of the glass and silica particles having a thin layer of carbohydrate covalently bonded thereto, the bonded phase supports preferably ranged in size from 5 to 128 microns and had pore diameters of a controlled porosity ranging from 40 to 1650 A and were packed into thick walled stainless steel, or other, tubing and connected to high pressure pumps with the column outlet being connected to an ultraviolet detector. All of the glass and silica bonded phase supports thus tested were capable of withstanding at least 3000 psig column head pressures without collapsing. While the phase supports might have been capable of withstanding still higher pressures, equipment availability prevented ascertaining the same.

From the foregoing it can be seen that the support of this invention provides a carbohydrate bonded on a controlled porosity column packing, and such a support may be used in chromatography columns operating at pressures at least to 3000 psig. This is at least 10 times greater pressure than any other known carbohydrate containing stationary phase has been able to withstand. The advantage gained by this mechanical stability is that separation speeds may be increased by 10 fold.

In addition, low molecular weight dextrans, dextrins, and glycidoxy silanes covalently bonded to silica surfaces have been successful in preventing adsorption of protein to silica surfaces. This enables obtaining higher recoveries of sensitive protein from controlled porosity glass columns.

The support of this invention is also particularly useful for high speed liquid chromatography and is felt to be the first use of a bonded phase carbohydrate ester column for high speed liquid chromatography. The polarity of the carbohydrate ester functional groups makes it useful in spearations in organic systems, and again the primary advantage of the column is speed. In addition, liquid-liquid partition chromatography utilizing underivatized carbohydrates on solid supports has also not been successful heretofore. The carboxymethyl dextran and tetrose amine bonded phase supports make possible high speed ion exchange chromatography of proteins which has heretofore not been possible. Finally, the hydrophobic dextran bonded phase support makes possible high speed hydrophobic chromatography of proteins which has not previously been possible.

In view of the foregoing, it is felt that the carbohydrate bonded phase support and method of forming the same as set forth herein provides an improved support suitable for enhanced useage of chromatographic systems.

What is claimed is:
1. A process for producing a bonded support for a chromatographic system, said process comprising:
   providing a porous inorganic support structure having available surface hydroxyl groups, said support structure having dimensions suitable for use as a support in a chromatographic system;
   bonding an organo silane onto said inorganic support structure; and
   covalently bonding a thin layer of carbohydrate material of less than about 30 A onto said organo silane whereby the formed support is mechanically stable with carbohydrate separation characteristics and is hydrophilic.
2. The process of claim 1 wherein said inorganic support structure provided is an alkyl amine treated support.
3. The process of claim 2 wherein said covalent bonding is by an amide bond formed by coupling through terminal carboxyl groups formed from dextran by oxidation to carboxylic acid.
4. The process of claim 3 wherein said coupling is carried out through carboxyl methyl dextran.
5. The process of claim 1 wherein said carbohydrate material is selected from saccharides having a molecular weight no greater than about 6000.
6. The process of claim 5 wherein said named group includes glycerol ethers, tetrose ethers, sorbitol, starch, dextrans, dextrins, carboxymethyl dextrans and polygalactan.

7. The process of claim 1 wherein said covalent bonding is by isourea bonding of said carbohydrate to said inorganic support.

8. The process of claim 7 wherein said inorganic support structure provided is an alkyl amine treated support and wherein said isourea bonding is formed by the steps of treating the carbohydrate with cyanogen bromide and then adding the solution to said alkyl amine treated support.

9. The process of claim 8 wherein said alkyl amine treated support is prepared by treating said support with an aqueous solution of γ-aminopropyl triethoxysilane at pH4 for 2 hours at a temperature of 90°C.

10. The process of claim 1 wherein said covalent bonding is by amine linkage of said carbohydrate to said inorganic support.

11. The process of claim 10 wherein said amine linkage is by schiff base coupling.

12. The process of claim 11 wherein said inorganic support structure provided is an alkyl amine treated support and wherein said schiff base coupling includes the steps of contacting an aqueous solution of said carbohydrate with said alkyl amine treated glass support, filtrating the same and then reducing the schiff base coupled carbohydrate on glass with $NaBH_4$ to a secondary amine.

13. The process of claim 10 wherein said inorganic support structure provided is an alkyl amine treated support and wherein a dialdehyde carbohydrate material selected from the group consisting of dialdehyde starch and dialdehyde dextran is coupled to said alkyl amine treated glass support by contacting said dialdehyde carbohydrate material and said alkyl amine glass support to form schiff base linkages, filtering the resulting material and reducing the schiff base linkages thereof to secondary amines by treatment with aqueous $NaBH_4$.

14. The process of claim 1 wherein said covalent bonding is by isourea linkage.

15. The process of claim 1 wherein said covalent bonding includes preparation of hydrophobic supports.

16. A support made in accordance with the method as defined in claim 1.

17. A process for producing a bonded support for a chromatographic system, said process comprising:
providing a porous inorganic support structure having available surface hydroxyl groups, said support structure having dimensions suitable for use as a support in a chromatographic system; and
covalently bonding a thin layer of glycidoxyl-propyl silane of less than about 30 A onto said inorganic support structure whereby the formed support is mechanically stable with good separation characteristics and is hydrophilic.

18. The process of claim 17 wherein said support treated with said glycidoxyl-propyl silane is hydrolyzed to form a hydrophillic glycerol bonded support.

19. A process for producing a bonded support for a chromatographic system, said support comprising:
providing a porous alkyl amine treated support structure having dimensions suitable for use in a chromatographic systems; and
covalently bonding a thin layer of carbohydrate material of less than about 30 A onto an organo silane which is in turn bonded onto said alkyl amine treated support to thereby form a mechanically stable support that has the separation characteristics of carbohydrates and is hydrophilic.

20. The process of claim 19 wherein said support is able to withstand pressures up to 3000 psig without collapsing.

21. A support material made in accordance with the method as defined in claim 19.

* * * * *